United States Patent
Hagelganz et al.

(10) Patent No.: US 8,235,714 B2
(45) Date of Patent: Aug. 7, 2012

(54) CONVERTIBLE BUCCAL TUBE ORTHODONTIC BRACKET

(75) Inventors: Rolf Hagelganz, Dundee, OR (US); Juergen Bathen, McMinnville, OR (US); Klaus Hagelganz, McMinnville, OR (US)

(73) Assignee: World Class Technology Corporation, McMinnville, OR (US)

(*) Notice: Subject to any disclaimer, the term of this patent is extended or adjusted under 35 U.S.C. 154(b) by 269 days.

(21) Appl. No.: 12/540,089

(22) Filed: Aug. 12, 2009

(65) Prior Publication Data

US 2011/0039225 A1 Feb. 17, 2011

(51) Int. Cl.
*A61C 3/00* (2006.01)

(52) U.S. Cl. ............................................ 433/13; 433/10

(58) Field of Classification Search ................... 433/8–21
See application file for complete search history.

(56) References Cited

U.S. PATENT DOCUMENTS

| | | | |
|---|---|---|---|
| 2,265,420 A * | 12/1941 | Brusse et al. | 433/11 |
| 3,391,461 A | 7/1968 | Johnson | |
| 3,838,514 A | 10/1974 | Polak | |
| 4,419,078 A | 12/1983 | Pletcher | |
| 4,498,867 A | 2/1985 | Kesling | |
| 4,634,662 A * | 1/1987 | Rosenberg | 433/10 |
| 4,820,151 A | 4/1989 | Pospisil | |
| 4,927,362 A | 5/1990 | Snead | |
| 5,059,119 A | 10/1991 | Snead | |
| 5,288,229 A | 2/1994 | Huff et al. | |
| 5,707,232 A | 1/1998 | Strauss et al. | |
| 6,142,775 A | 11/2000 | Hansen et al. | |
| 6,168,429 B1 * | 1/2001 | Brown | 433/11 |
| 6,217,322 B1 | 4/2001 | Kesling | |
| 6,217,332 B1 * | 4/2001 | Kumar | 433/173 |
| 6,428,314 B1 | 8/2002 | Jones, Jr. et al. | |
| 6,705,862 B2 * | 3/2004 | Schultz | 433/17 |
| 6,843,651 B2 | 1/2005 | Orikasa | |
| 6,887,075 B2 * | 5/2005 | Kawaguchi et al. | 433/17 |
| 7,134,873 B2 * | 11/2006 | Miyaji et al. | 433/10 |
| 7,210,927 B2 * | 5/2007 | Abels et al. | 433/10 |
| 2003/0186185 A1 | 10/2003 | Schultz | |
| 2006/0003282 A1 * | 1/2006 | Nicholson | 433/11 |
| 2006/0014116 A1 | 1/2006 | Maijer et al. | |
| 2006/0172248 A1 * | 8/2006 | Sernetz et al. | 433/8 |
| 2007/0264606 A1 * | 11/2007 | Muha et al. | 433/17 |
| 2009/0162807 A1 | 6/2009 | Hagelganz et al. | |

OTHER PUBLICATIONS

Lee S. Young, International Search Report [Form PCT/ISA/210] (application # PCT/US10/01986), Sep. 15, 2010, pp. 1-2.
Lee S. Young, Opinion of the International Searching Authority [Form PCT/ISA/237] (application # PCT/US10/01986), Sep. 8, 2010, pp. 1-4.

* cited by examiner

*Primary Examiner* — Cris L Rodriguez
*Assistant Examiner* — Edward Moran
(74) *Attorney, Agent, or Firm* — Chernoff, Vilhauer, McClung & Stenzel, LLP

(57) ABSTRACT

An orthodontic bracket having a base attachable to a tooth surface, with the base extending outward away from the tooth surface and forming an archwire slot sized to receive an archwire therewithin, and a removable archwire slot cover coined onto the base so as to cover the archwire slot and enable the bracket to function as a buccal tube when the cover is attached. The cover may be removed from the bracket base without removal of the bracket from the tooth surface so as to provide an open archwire slot for continued orthodontic treatment subsequent to removal of the removable archwire slot cover.

11 Claims, 6 Drawing Sheets

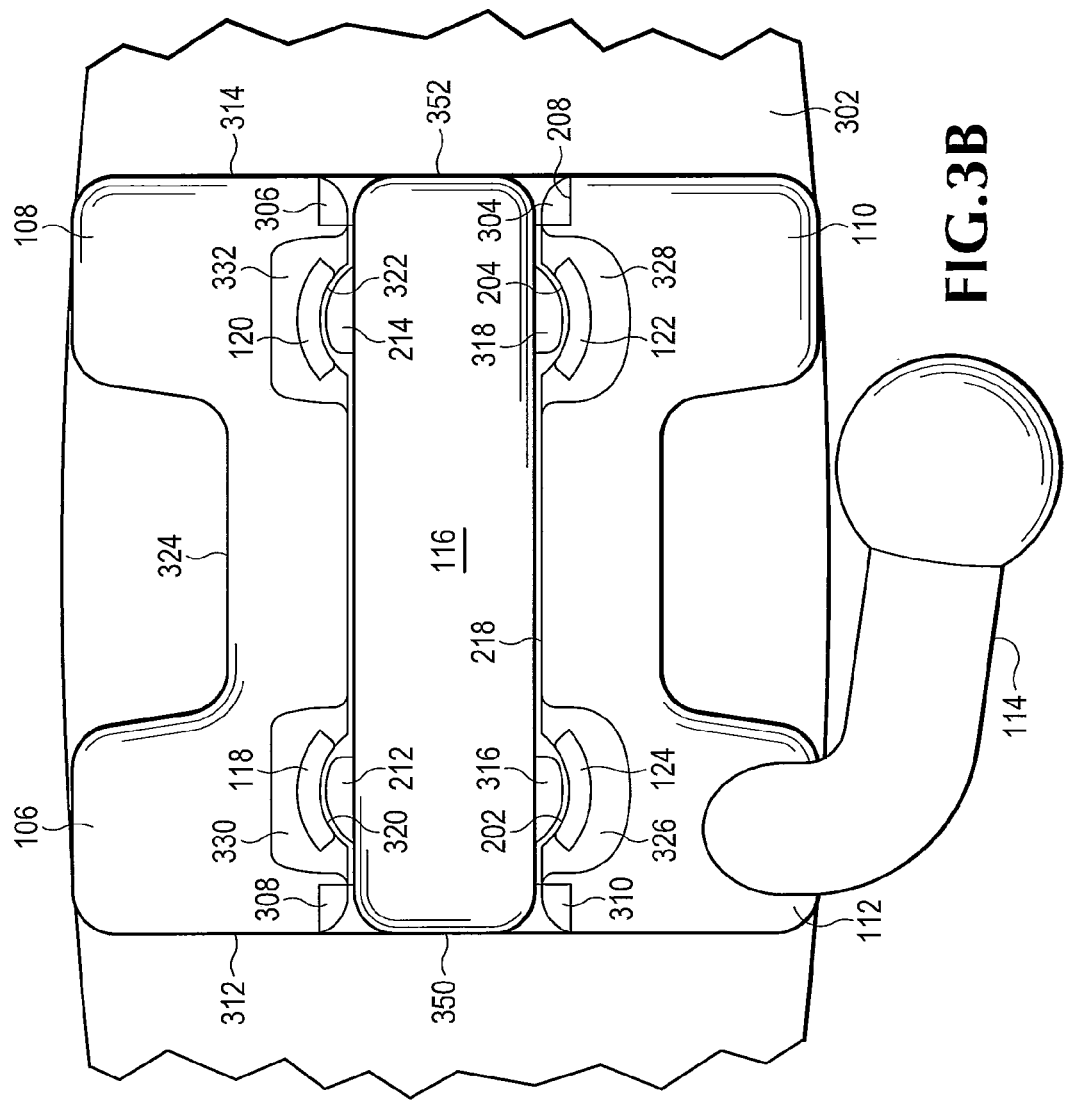

CONVERTIBLE BUCCAL TUBE ORTHODONTIC BRACKET

BACKGROUND OF THE INVENTION

This disclosure relates to orthodontic brackets, and, more particularly, to orthodontic brackets configured for initial use as buccal tubes and each having a removable cover for retaining an archwire within an archwire slot and allowing the bracket to function as a conventional bracket with an open archwire slot when the cover is removed.

Orthodontic treatment generally comprises dental work to correct irregularities of the teeth or of the relation of the teeth to surrounding anatomy. The irregularities may involve malocclusions with varying degrees of severity. Class 1 malocclusions, for example, may involve spacing irregularities such as excessive crowding or diastema (a gap between two adjacent teeth). Class 2 malocclusions may involve overbite conditions where the upper anterior teeth project labially over the lower anterior teeth. Class 3 malocclusions, in contrast, may involve underbite conditions where the upper anterior teeth close within the lingual side of the lower anterior teeth. For these and other observed irregularities, treatment typically involves installation of braces or mechanical aids for repositioning the teeth into correct orthodontic alignment.

Braces generally include orthodontic brackets configured for attachment to the labial or lingual surfaces of the teeth or for attachment to metallic bands secured around the teeth. The brackets typically include archwire slots within which a flexible yet resilient archwire may be engaged. Each bracket is typically bonded to the tooth surface so that the bracket's archwire slot is oriented for engagement with the archwire. Various techniques are used for orienting the brackets. For example, an edgewise appliance comprises braces whereby each bracket is oriented and bonded to the tooth so that the archwire slot is perpendicular to the long axis of the root of the tooth. Alternatively, a straight-wire appliance includes braces whereby each bracket is oriented and bonded to the tooth so that the archwire slot is parallel to the occlusal plane (the plane of the biting surfaces of the teeth).

The archwire is typically a curved metallic wire having a rectangular or circular cross section that is bent or twisted prior to engagement with the brackets. The memory or restoring force exerted by the archwire upon the brackets serves to move the teeth into the desired alignment. Throughout the duration of orthodontic treatment, the orthodontist periodically adjusts the shape of the archwire (as well as the configuration of other attachments such as elastic bands and so forth) to achieve the correct orthodontic alignment.

The orthodontic brackets most commonly used on the teeth along the dental arch incorporate tie wings or extensions that project upwardly and downwardly in a gingival-occlusal orientation and require the use of ligatures or ligating modules to hold the archwire within the archwire slots. The ligatures or ligating modules are typically donut-shaped elastomeric rings or wires that are stretched around or twisted around the tie wings.

The distal ends of the archwire are typically anchored at each end of the dental arch in an orthodontic bracket commonly referred to as a buccal tube, which is attached to the surface of a terminal or anchor tooth. A buccal tube generally provides an anchor or termination of one of the (two) distal ends of an archwire when the archwire is in position, generally spanning the dental arch from the rear molars on one side mesially toward the sagittal plane (or midline of the face) and then distally toward the rear molars on the other side. A buccal tube generally provides a tubular opening that is typically substantially rectangular in cross section within which an end of an archwire may be inserted.

Anchor teeth are typically the rearmost molars in the dental arch and are most commonly the first (or six-year) molars during initial orthodontic treatment. Once the patient's second pair of rear molars (or twelve-year molars) fully erupt and become available as anchor teeth, the dentist may desire to include those newly erupted molars into orthodontic treatment by using them as anchor teeth and changing or converting the buccal tubes on the first molars to orthodontic brackets having open archwire slots.

Convertible buccal tube brackets are available which are intended to eliminate the need for removal of the buccal tube brackets and mounting of replacement open archwire slot brackets on the same molars. Thus, the successful use of convertible buccal tube brackets may eliminate potential damage to the molar enamel, reduce patient chair time, and reduce the cost of orthodontic treatment.

Several different convertible buccal tube orthodontic brackets have been designed. However, most of those have less-than-desirable designs, incorporating features requiring prohibitively expensive machining operations or comprising multiple separate parts, which in turn increases the number of failure modes and disadvantages with such brackets. Other designs have been rejected in the marketplace due to poor quality or poor design, a lack of available features, difficulty of use, or other factors.

What is needed, therefore, is a convertible buccal tube orthodontic bracket that incorporates a removable archwire slot cover and that offers a different style of bracket than those available today.

The foregoing and other objectives, features, and advantages of the invention will be more readily understood upon consideration of the following detailed description of the invention taken in conjunction with the accompanying drawings.

BRIEF DESCRIPTION OF THE SEVERAL DRAWINGS

For a more complete understanding of the present invention, the drawings herein illustrate examples of the invention. The drawings, however, do not limit the scope of the invention. Similar references in the drawings indicate similar elements.

FIGS. 3A and 3B are a top views of the convertible buccal tube orthodontic bracket in FIG. 1, according to various embodiments.

DETAILED DESCRIPTION OF PREFERRED EMBODIMENTS

In the following detailed description, numerous specific details are set forth in order to provide a thorough understanding of the present invention. However, those skilled in the art will understand that the present invention may be practiced without these specific details, that the present invention is not limited to the depicted embodiments, and that the present invention may be practiced in a variety of alternate embodiments. In other instances, well known methods, procedures, components, and systems have not been described in detail.

Various operations will be described as multiple discrete steps performed in turn in a manner that is helpful for understanding the present invention. However, the order of description should not be construed as to imply that these operations are necessarily performed in the order they are presented, nor even order dependent.

Figure 1:
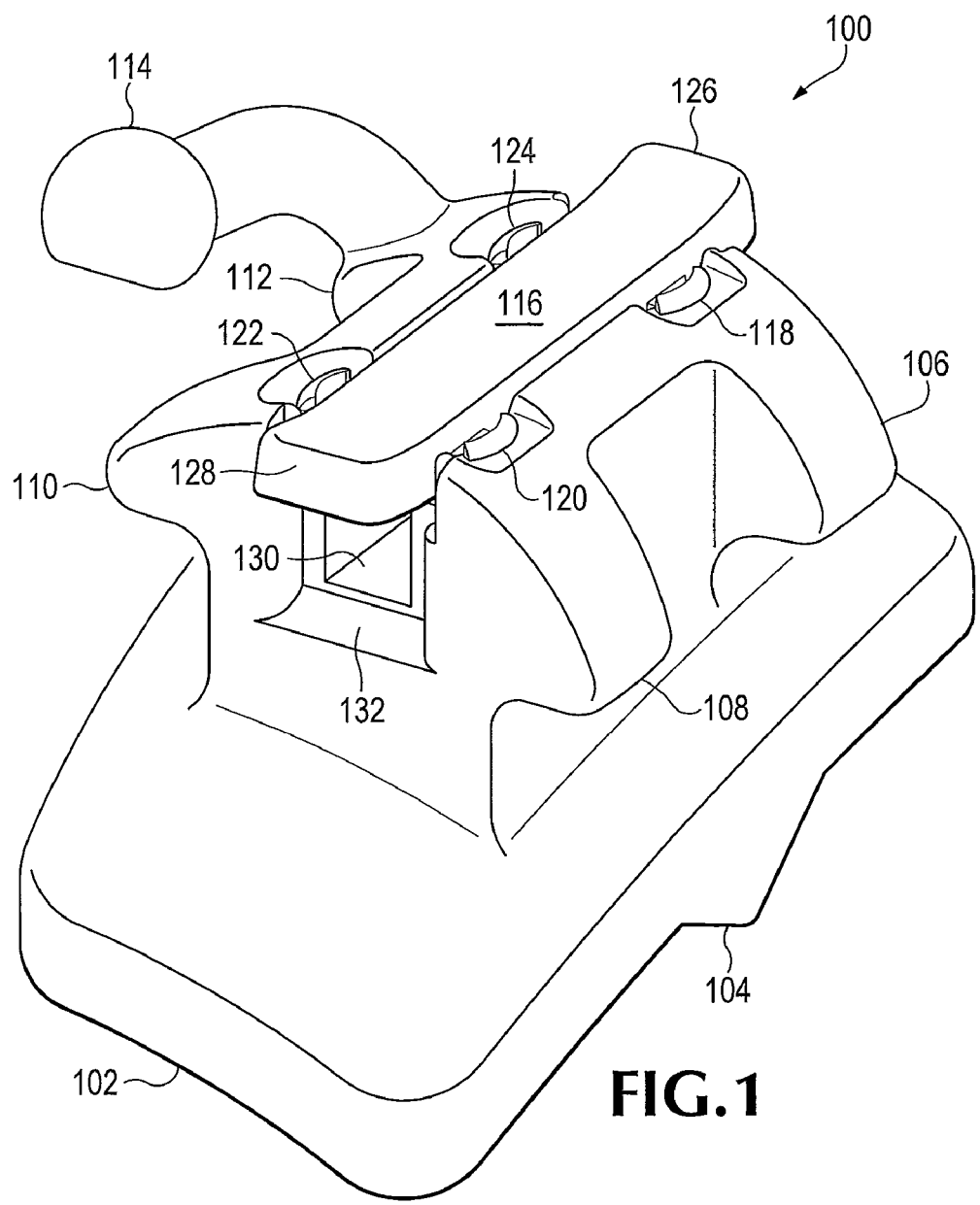
FIG. 1 is a perspective view of an exemplary convertible buccal tube orthodontic bracket, according to one embodiment.
Figure 2:
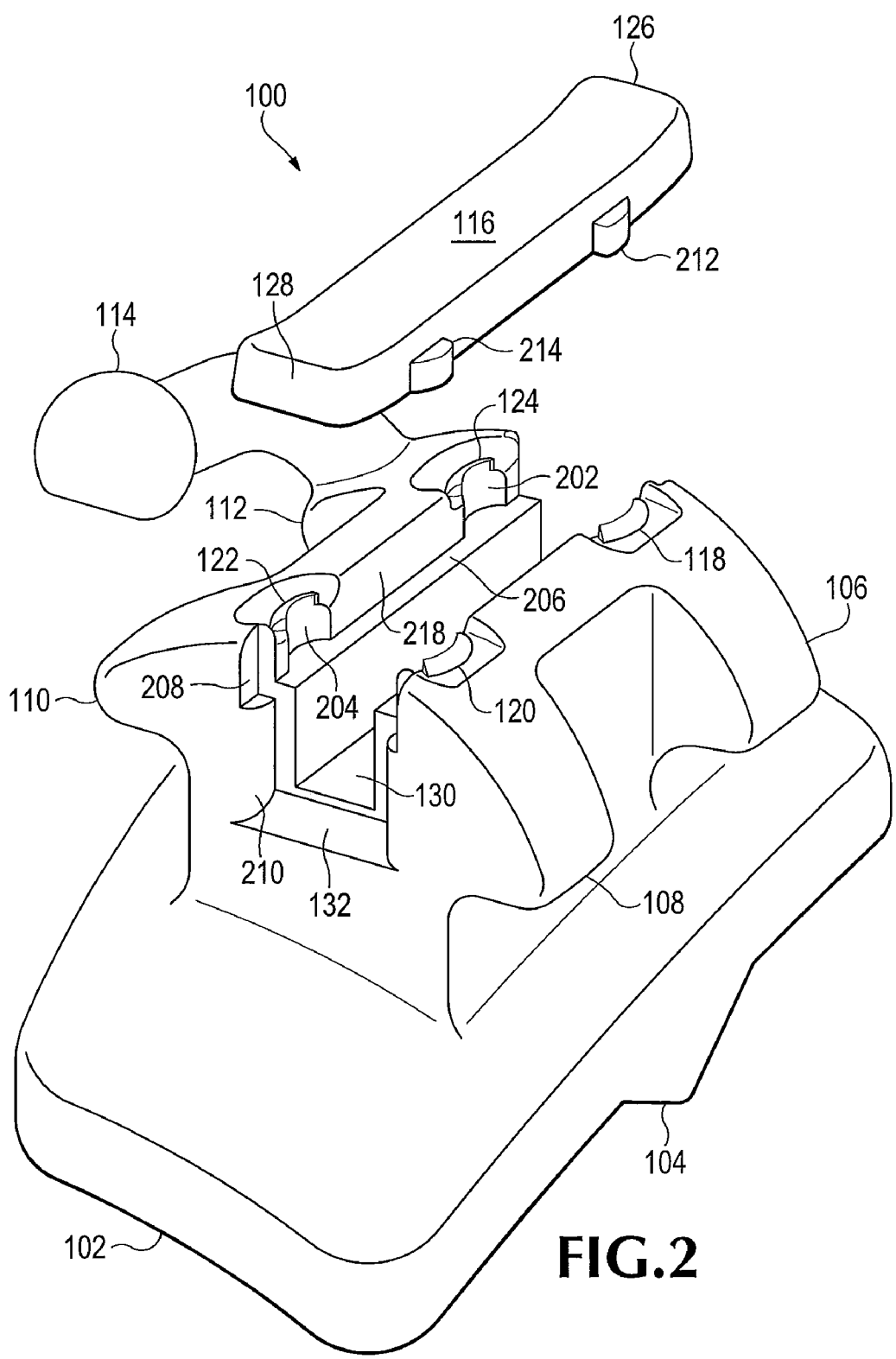
FIG. 2 is a perspective view of the convertible buccal tube orthodontic bracket in FIG. 1 shown with its removable cover not yet positioned for attachment over the archwire slot, according to one embodiment.
Figure 5:
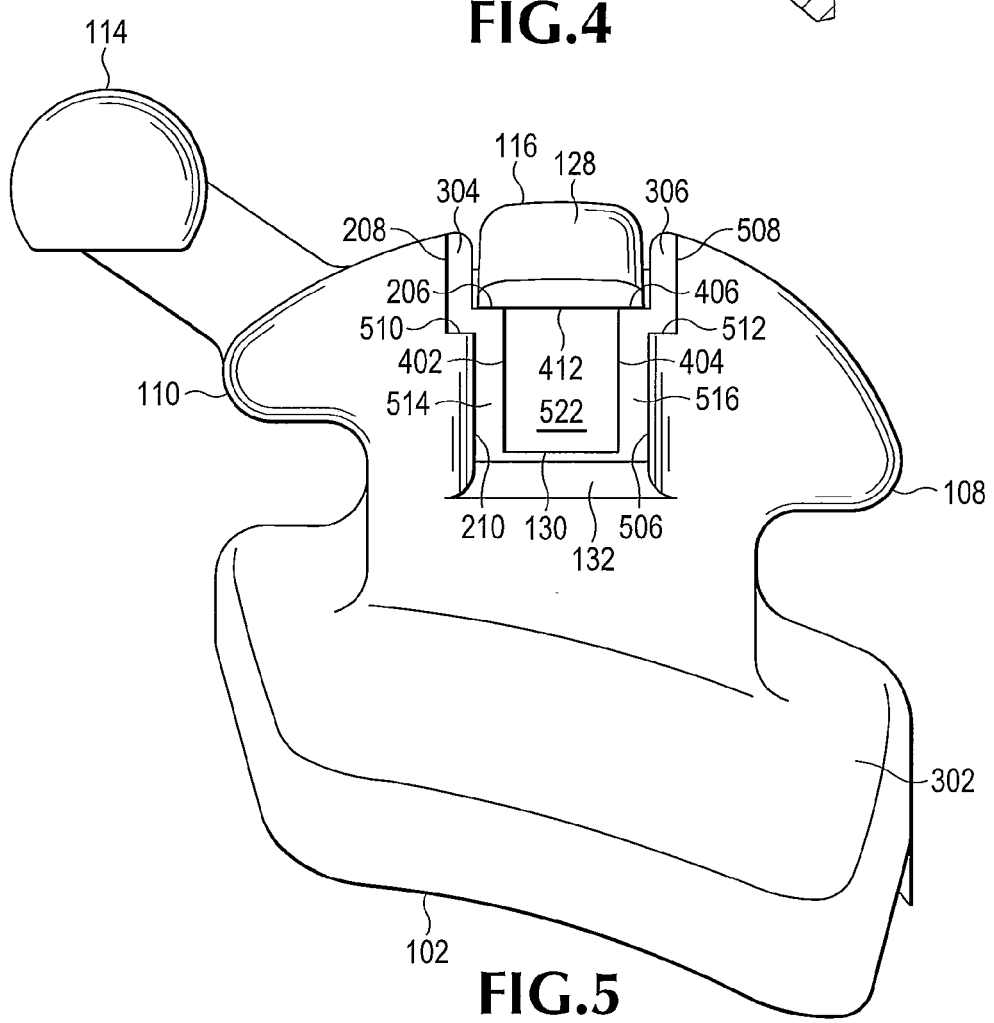
FIG. 5 is an end view of the convertible buccal tube orthodontic bracket in FIG. 1, according to one embodiment.
Figure 6:
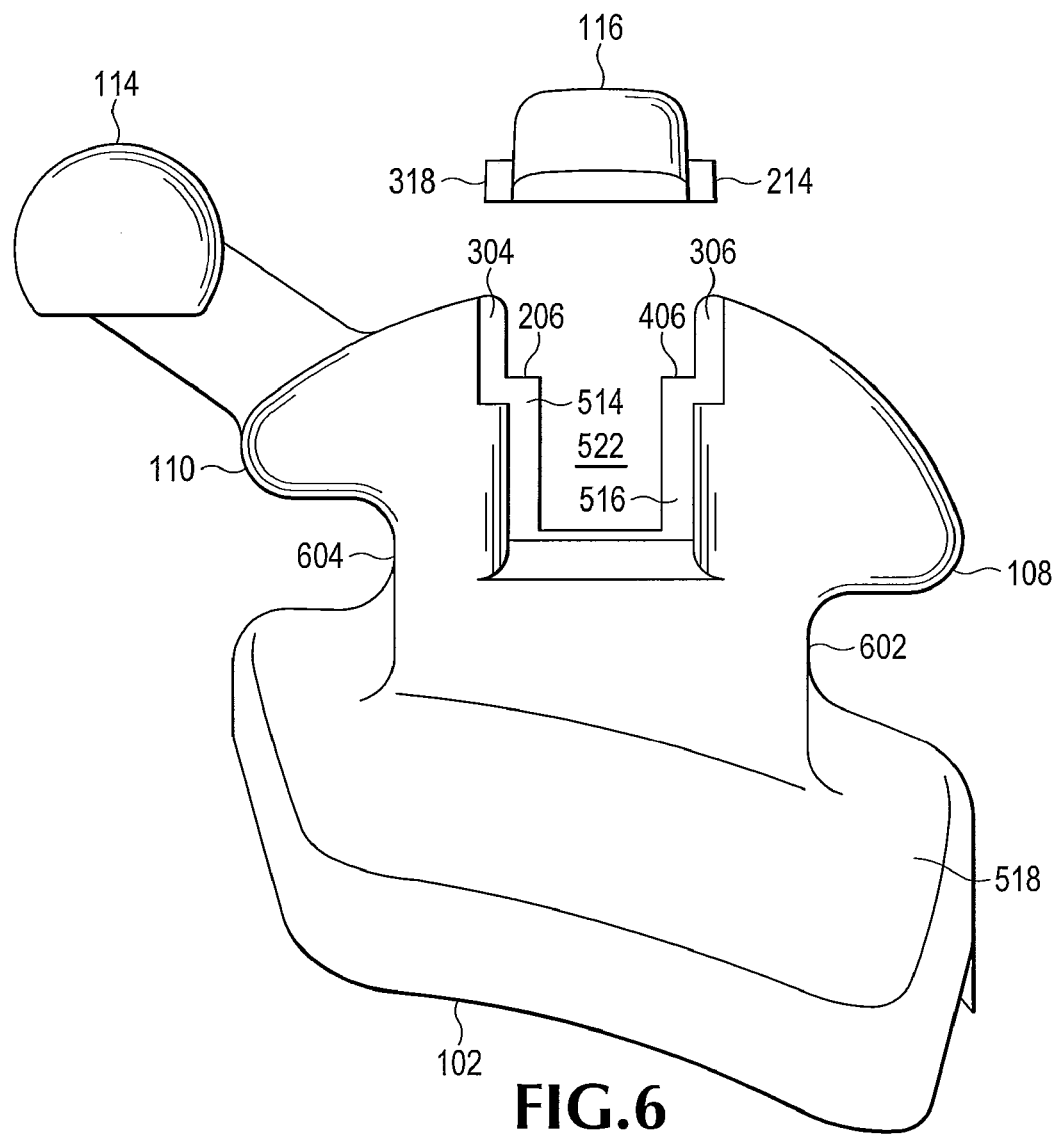
FIG. 6 is an end view of the convertible buccal tube orthodontic bracket of FIG. 1 shown with its removable cover not yet positioned for attachment over the archwire slot, according to one embodiment.

By way of general overview and as shown in the perspective view in FIG. 1 and also the end view in FIG. 5, the exemplary convertible tube orthodontic bracket 100, according to a preferred embodiment, has a base 102 attachable to a tooth surface (not shown) with the base 102 extending outward away from the tooth surface forming an archwire slot 522 sized to receive an archwire (not shown) therewithin. A removable archwire slot cover 116 is preferably coined onto the base 102 so as to cover at least a portion of the archwire slot 522 and enable the bracket 100 to function as a buccal tube. The removable archwire slot cover 116 is preferably capable of being removed from the bracket base 102 without removal of the bracket 102 from the tooth surface so as to provide an open archwire slot (as shown in FIGS. 2 and 6) for continued orthodontic treatment subsequent to removal of the removable archwire slot cover 116.

Coining is generally a closed-die forging operation, typically performed cold, in which the workpiece is subjected to such force as to cause the material to have a plastic consistency, allowing it to flow into the small details of the die. As used herein, however, the terms coin, coined, and coining refer more broadly to a process of mechanically forcing material into a desired shape and orientation. Preferably, the removable archwire slot cover 116 is coined onto the base 102 such that the outward surface of the coined material is a well-defined imprint of the die. Also preferably, the coining results in smooth outward surfaces of the coined material. In less preferred embodiments, however, such coining may result in less well-defined outward surface detail. In some embodiments, such coining may comprise mechanically forcing enough material into a shape and orientation to provide sufficient retention of the removable archwire slot cover 116. Further, in some embodiments, such coining may comprise bending, crimping, or otherwise moving material on the base 102 to sufficiently retain portions of the removable archwire slot cover 116.

Preferably, at least a portion of material comprising the base 102, such as, for example, one or more of the outward protrusions 118, 120, 122, 124, is coined inward toward a bottom surface 130 of the archwire slot 522 and over at least a portion of material comprising the removable slot cover 116 (for example, as shown in the cross sectional view in FIG. 4) so as to securably attach the removable archwire slot cover 116 to the base 102 and to sufficiently cover the archwire slot 522, enabling the bracket 100 to function as a buccal tube. The removable archwire slot cover 116 is preferably removable from the base 102 by applying sufficient force to the removable archwire slot cover 116 in a direction away from the bottom surface 130 of the archwire slot 522 to overcome and thereby dislodge at least a portion of material comprising the base 102 that is coined over at least a portion of material comprising the removable archwire slot cover 116.

In preferred embodiments, the bracket 100 includes at least one pair of tie wings, such as, for example, tie wings 108 and 110, with each of pair of tie wings having a first tie wing (i.e. tie wing 108) and a second tie wing (i.e. tie wing 110) oriented on opposite sides of the archwire slot 522 from one another and each extending transversely away from the archwire slot 522. The first and second tie wings (i.e. tie wings 108 and 110, respectively) are preferably oriented and formed so as to permit use of a ligature or ligating module for holding an archwire (not shown) within the archwire slot 522 when the removable archwire slot cover 116 is removed. For example, as shown in the end view in FIG. 6, the tie wings 108 and 110 extend away from the archwire slot 522 so as to provide retention of a ligature or ligating module (not shown) to within the narrower width area between base sidewalls 602 and 604 that is below the tie wings 108 and 110 and above the lower portion 518 of the bracket.

As shown in FIG. 1, the bracket 100 includes two pairs of tie wings (or double tie wings)—a pair of tie wings 108, 110 at one end of the bracket 100 and another pair of tie wings 106, 112 at the other end of the bracket 100. Double tie wings are typically used due to the improved visibility and easier manipulation of ligatures or ligating modules used. For example, the bracket shown in the top view in FIG. 3A has two tie wings 108 and 110 on one side of the archwire slot 522 and provides visibility of and access to any ligature or ligating module seated in the narrower width area 324 which corresponds to the base sidewall 602 shown in the end view in FIG. 6. However, more or less pairs of tie wings may be incorporated or the number of tie wings on a given side of the archwire slot 522 may be different (i.e. the tie wings need not be in pairs). For example, the tie wings 108 and 106 on one side of the archwire slot 522 may form a single tie wing having an end profile as for the tie wing 108 in FIG. 6. Likewise, the tie wings 110 and 112 on the other side of the archwire slot 522 may form a single tie wing having an edge profile as for the tie wing 110 in FIG. 6.

Irrespective of the number of pairs of tie wings, the operation of a ligature or ligating module is generally the same. The ligature or ligating module may be positioned downward over a bracket having an archwire seated within the archwire slot and then wrapped downward under the ends of the tie wings so that the ligature or ligating module holds the archwire in the archwire slot of the bracket.

Figure 3A:
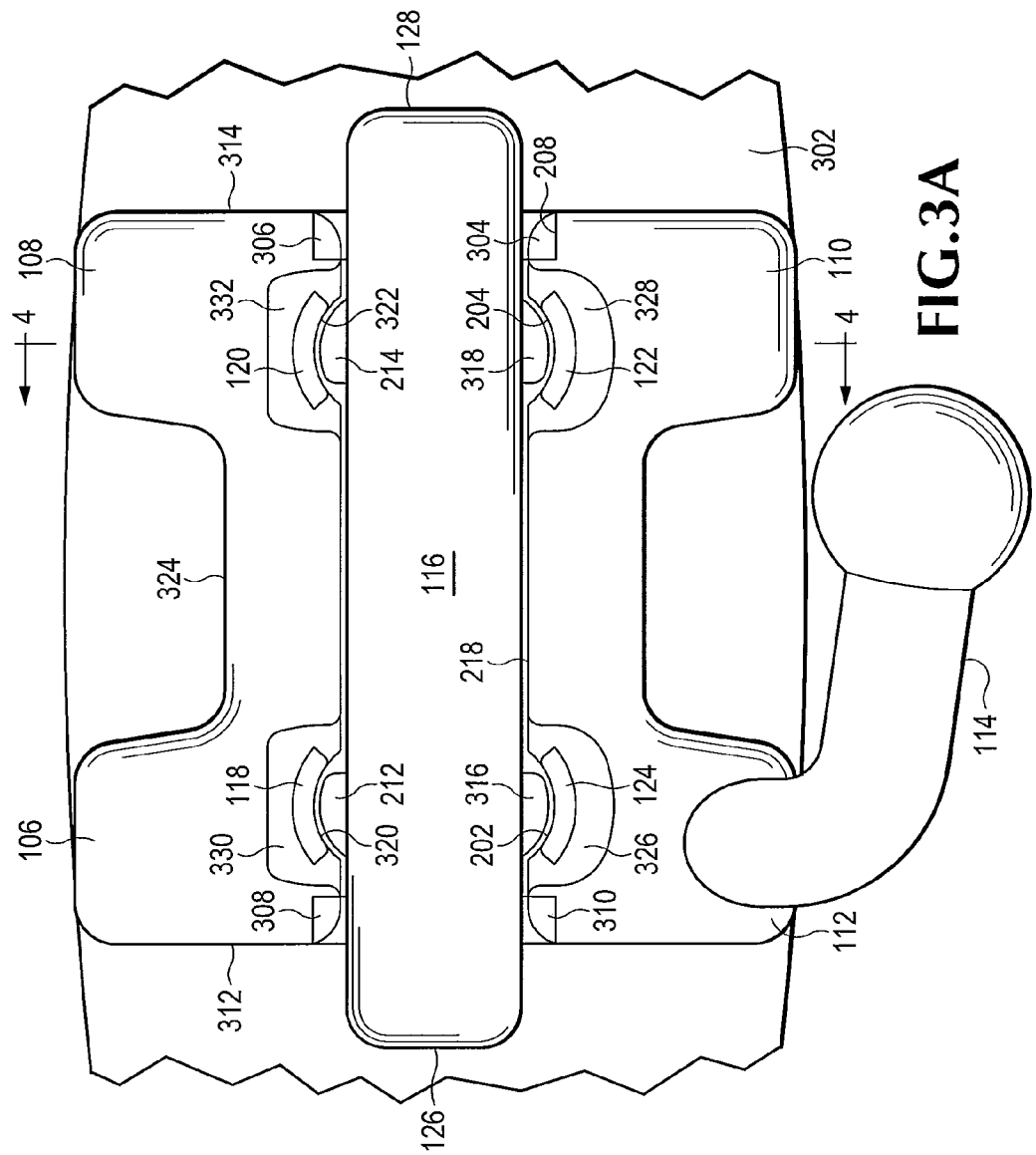

As previously mentioned, FIG. 1 shows a convertible buccal tube orthodontic bracket 100 configured to function as a buccal tube bracket with its removable archwire slot cover 116 coined over the archwire slot 522. The removable archwire slot cover 116 is shown (as preferred) completely covering the archwire slot 522, but this need not be the case. The removable archwire slot cover 116 may cover less than the complete longitudinal length of the archwire slot 522. Preferably, however, the removable archwire slot cover 116 extends longitudinally over and beyond the open ends of the archwire slot 522. FIG. 3A depicts the ends 126 and 128, respectively, of the removable archwire slot cover 116 extending beyond the edges 312 and 314, respectively which are even with the open ends of the archwire slot 522. FIG. 3B depicts another embodiment in which the ends 350 and 352, respectively, of the removable archwire slot cover 116 extend up to and even (i.e. flush) with the edges 312 and 314, respectively which are even with the open ends of the archwire slot 522. The present inventor discovered that extending the removable archwire slot cover 116 beyond the open ends of the archwire slot 522 facilitates easier use of the bracket as a buccal tube and also subsequent removal of the removable archwire slot cover 116. The additional material overhanging the slot opening provides a guide for easier insertion of the distal end of an archwire as well as additional material for easier gripping, manipulation, and leverage for subsequent removal of the cover 116.

FIG. 1 further illustrates the ends 126 and 128 of the removable archwire slot cover 116 as being flared outward away from the bottom surface 130 of the archwire slot 522. The present inventor discovered that incorporating the outwardly flared ends of the removable archwire slot cover 116 improves the ease of using the bracket 100 as a buccal tube because the outward flaring provides lead-in contours or guides (together with archwire slot lead-in chamfers 132, 210, and 506 (and their oppositely oriented chamfers, not shown) for easier insertion of the distal end of an archwire. The present inventor further discovered that incorporating the outwardly flared ends of the cover 116 further improves the ease of gripping and manipulation when subsequently removing the cover 116 to convert the buccal tube into an open archwire slot orthodontic bracket. The flared ends 126 and 128 increases the room between the underside of the cover 116 (at the ends 126 and 128) and the lower portion 302 of the bracket 100.

FIGS. 1-3A, 3B, and 5-6 show embodiments of the bracket 100 having a ball hook 114, and FIGS. 1-2 and 5-6 show embodiments of the bracket 100 having a molar-conforming downward surface protrusion 104 in the base 102. Those features may or may not be incorporated into the bracket 100 and are included in the drawings as exemplary features and for relational reference between the different views shown. Other features not shown in the drawings may be incorporated into the bracket 100.

Whereas FIG. 1 is a perspective view of the bracket 100 with the removable archwire slot cover 116 placed over the archwire slot 522 (but not yet securely coined onto the bracket), FIG. 2 is a perspective view of the bracket 100 with the removable archwire slot cover 116 shown lifted outward away from the bottom 130 of the archwire slot 522 to illustrate preferred features of the removable archwire slot cover 116 and corresponding features on the bracket base. As shown in perspective view in FIG. 2 together with the top view in FIGS. 3A, the removable archwire slot cover 116 includes one or more tabs such as tabs 212, 214, 316, and 318 oriented transversely to the archwire slot 522 over which material of the base, such as outward protrusions 118, 120, 124, and 122, respectively, may be coined so as to retain the removable archwire slot cover 116 over the archwire slot 522. The base preferably includes one or more cutouts such as cutouts 320, 322, 202, and 204 which cooperatively mate with one or more tabs, such as tabs 212, 214, 316, and 318, respectively.

Four substantially semi-circular shaped tabs 212, 214, 316, and 318 are shown in FIG. 3A extending transversely from the sides of the removable archwire slot cover 116, however a different number and configuration of tabs may be used. For example, tabs 212 and 214 are shown as separate substantially semi-circular material extensions spaced away from one another longitudinally along one side of the cover 116. Instead, the tabs 212 and 214 may be differently shaped, such as substantially rectangular in shape, or such tabs may be connected together as a single ridge extending from the side of the cover 116. The corresponding cutouts 320 and 322 are preferably sized to receive the respective tabs 212 and 214. If the tabs 212 and 214 comprise, for example, a single ridge of material, then the corresponding cutouts 320 and 322 may be sized accordingly to receive such a ridge. In a less preferred embodiment, a single region of material extending transversely from just one side of the cover 116 may be used together with a corresponding cutout and protrusion of material on the bracket base sufficiently sized so as to securely but removably hold the cover 116 over the archwire slot 522. In such an embodiment the single region of material may be larger than any one of the tabs 212, 214, 316, or 318, and/or the material protrusion to be coined over the single region of the cover 116 may be larger than any one of the outward protrusions 118, 120, 124, or 122 so as to provide enough retention force to securely but removably hold the cover 116 over the archwire slot 522.

Preferably each of the four tabs 212, 214, 316, and 318 and corresponding outward material protrusions 118, 120, 124, and 122, respectively, are oriented as shown in FIGS. 1-3A within depressed areas 330, 332, 326, and 328, respectively, to facilitate coining of the removable archwire slot cover 116 onto the bracket 100. As shown, the outward surfaces of the depressed areas 330, 332, 326, and 328 are preferably substantially even (i.e. coplanar) with the outward surfaces of the respective tabs 212, 214, 316, and 318 so that the material coined inward toward the bottom 130 of the archwire slot 522 remains within the depressed areas and within controlled surface boundaries during the coining process. Further, the depressed areas 330, 332, 326, and 328 are preferably sufficiently oriented (depressed) toward the bottom 130 of the archwire slot 522 that the material portions coined over the cover 116 are less inclined to extend outward beyond the outward most surfaces of the bracket when the cover 116 is removed. As shown in FIG. 1, for example, the outward protrusions 118, 120, 122, and 124 (shown before coining) remain within the depressed areas and below the outward most surfaces of the bracket 100. When the cover 116 is coined onto the bracket base as shown in FIG. 4 and then subsequently removed, the coined over material (i.e. 122 and 120 shown in FIG. 4) remains substantially within the depressed areas (i.e. 328 and 332, respectively).

Figure 4:
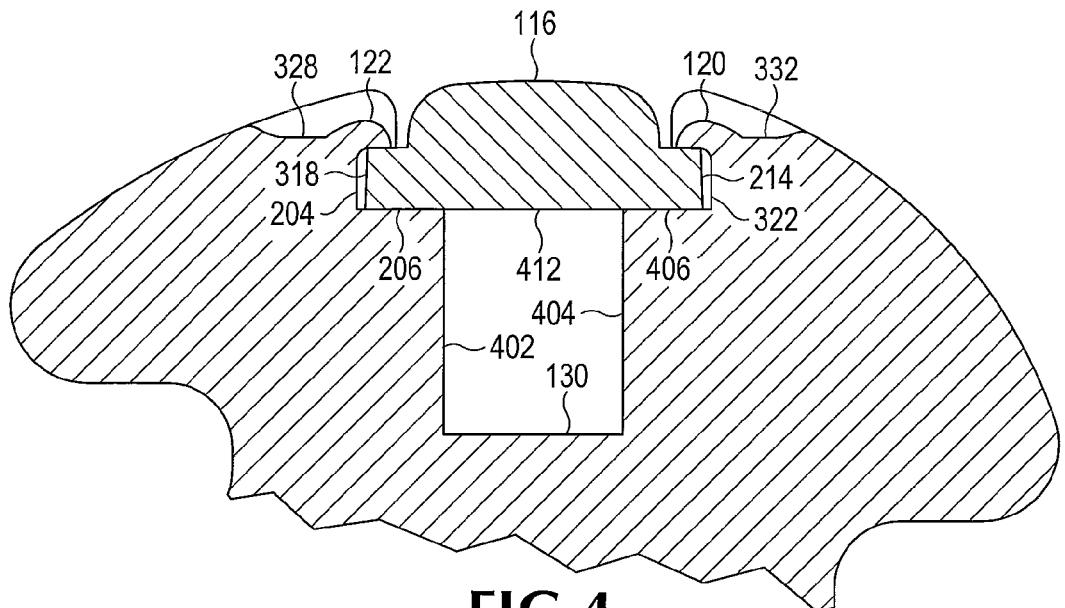
FIG. 4 is a sectional view of the convertible buccal tube orthodontic bracket at the cut line 4-4 indicated in FIGS. 3A and 3B, according to one embodiment.

The sectional view in FIG. 4 of the convertible buccal tube orthodontic bracket at the cut line 4-4 indicated in FIGS. 3A and 3B shows the removable archwire slot cover 116 coined onto the base 102, according to one embodiment. As shown, base material comprising the outward protrusions 122 and 120 is preferably coined (or made to exhibit plastic flow) so as to cover enough of the removable slot cover 116 (or portions or extensions thereof) to hold the cover 116 over the archwire slot 522. In FIG. 4, material comprising outward protrusions 122 and 120 is shown coined downward so as to capture and hold tabs 318 and 214. The present inventor discovered and invented coining a removable archwire slot cover onto an open archwire slot orthodontic bracket as described and illustrated, providing a convertible buccal tube orthodontic bracket different than those previously attempted.

The removable archwire slot cover 116 is shown covering the archwire slot 522, with the underside 412 of the cover 116 forming the outward surface within the covered slot. Although the sides 402 and 404 together with the bottom 130 and cover underside 412 preferably form a substantially rectangular cross section for the covered slot (or buccal tube), different cross sections may be used. For example, sides 402 and 404 may be angled so as to form a trapezoidal cross section.

The removable archwire slot cover 116 preferably rests not only on the one or more cutouts corresponding with the tabs formed on the cover 116 but also on longitudinal ledges 206 and 406 just above both sides 402 and 404 of the archwire slot 522. The ledges 206 and 406 are preferably substantially as shown in FIGS. 2 and 4-6 but may be of different widths or altogether omitted in lesser preferred embodiments. Preferably the ledges 206 and 406 are formed below the outward most surfaces of the bracket 100 so as to have slot-facing side walls, such as side wall 218 shown in FIG. 2, of substantially the same thickness as the cover 116.

Also shown in the several figures are corner cutouts (or notches) 304, 306, 308, and 310. For example, as indicated in FIG. 3A and again in FIG. 5, the corner cutout 304 results in a slot-facing surface 208 and an outward-facing surface 510. In similar fashion the corner cutout 306 results in a slot-facing surface 508 and an outward-facing surface 512. The corner cutouts 304 and 306 also result in end-facing surfaces 514 and 516, respectively, which are shown contiguous extending downward toward the toot surface mounting portion of the base 102, as shown. Although the corner cutouts and chamfers and end surfaces shown primarily in FIG. 5 are preferably as shown in the figures herein, such cutouts and end surfaces and chamfers may be differently oriented or even omitted in less preferred embodiments.

In one embodiment, slot width (which is the distance between archwire slot side walls 402 and 404) may be 0.0225 inches, slot depth (which is the distance between the underside 412 and the bottom 130) may be 0.029 inches, and the longitudinal length between edges 312 and 314 may be 0.126 inches. In another embodiment, slot width may be 0.0188 inches and slot depth may be 0.026 inches.

The orthodontic bracket described herein may comprise any of a wide variety of materials suitable for use in an orthodontic appliance. Such materials have commonly included plastics, ceramics, stainless steel, titanium, or other metal alloys. The bracket preferably comprises a biocompatible material with corrosion resistive properties, and the bracket preferably comprises materials which may be formed into the structures shown yet maintain suitable strength characteristics for retaining commonly used orthodontic archwires or other components of an orthodontic appliance.

Nickel may be the most common metal associated with contact dermatitis in orthodontics. Recent figures suggest that perhaps 10% of patients are sensitive to nickel. Nevertheless, nickel-containing metal alloys, such as nickel-titanium and stainless steel, are widely used in orthodontic appliances. Nickel-titanium alloys may have nickel contents above 50% and may potentially release enough nickel in the oral environment to elicit manifestations of an allergic reaction. Stainless steel has a much lower nickel content, perhaps around 8%, and, because the nickel is bound in a crystal lattice within stainless steel, the nickel may be less available to react. Consequently, stainless steel orthodontic components may be less likely to cause nickel hypersensitivity.

However, because of the remaining uncertainty regarding a particular patient's sensitivity to nickel, it may be desirable to provide nickel-free orthodontic brackets to avoid nickel hypersensitivity altogether. Therefore, the orthodontic bracket described herein preferably comprises a nickel-free material. In one embodiment, the bracket comprises a nickel-free cobalt-chromium alloy.

Several methods may be used to manufacture the orthodontic bracket described herein. For example, the bracket may be cast, machined, injection molded and so on. Injection molding of plastics may be used as may be ceramic injection molding (CIM) or metal injection molding (MIM) depending upon the materials chosen. The bracket preferably comprises a molded base coupled with a molded removable archwire slot cover that is coined to hold the cover onto the bracket (covering the archwire slot). A ball hook, or other components, may be welded to the bracket assembly or formed as part of the bracket body (i.e., as part of the molded bracket body).

The terms and expressions which have been employed in the forgoing specification are used therein as terms of description and not of limitation, and there is no intention in the use of such terms and expressions of excluding equivalence of the features shown and described or portions thereof, it being recognized that the scope of the invention is defined and limited only by the claims which follow.

What is claimed is:

1. An orthodontic bracket having
   (a) a base attachable to a tooth surface and having an archwire slot sized to receive an archwire said base having lateral cutout portions,
   (b) a removable archwire slot cover having laterally extending tabs adapted to matingly fit within said lateral cutout portions in said base so as to cover at least a portion of said archwire slot and to enable said bracket to function as a buccal tube, said removable archwire slot cover capable of being removed from said bracket base without removal of said bracket from said tooth surface so as to provide an open archwire slot for continued orthodontic treatment subsequent to removal of said removable archwire slot cover, and
   (c) a plurality of bendable protrusions formed in said lateral cutout portions of said base and selectively bendable toward and away from said archwire slot, said bendable protrusions being bent to bear against said tabs of said slot cover to retain said slot cover in said base.

2. The bracket of claim 1 wherein said removable archwire slot cover extends longitudinally over and beyond the open ends of said archwire slot.

3. The bracket of claim 1 wherein said base includes at least one pair of tie wings, each of said pair of tie wings having a first tie wing and a second tie wing oriented on opposite sides of said archwire slot from one another and each extending transversely away from said archwire slot, said first and second tie wings oriented and formed so as to permit use of a ligature or ligating module for holding said archwire within said archwire slot when said removable archwire slot cover is removed.

4. The bracket of claim 1 where said base includes one or more lead-in chamfers to said archwire slot.

5. The bracket of claim 1 wherein longitudinally opposite ends of said removable archwire slot cover are flared outward away from a bottom surface of said archwire slot.

6. The bracket of claim 1 wherein said removable archwire slot cover is positioned on at least one ledge formed upon said base so as to define an enclosed buccal tube sized to receive said archwire.

7. An orthodontic bracket comprising:
   (a) a base attachable to a tooth surface and extending outward away from said tooth surface said base including lateral cutout portions;
   (b) an archwire slot formed within said base and sized to receive an archwire therewithin, said archwire slot having a bottom and two opposing sides adjacent said bottom and extending longitudinally between two opposite ends;
   (c) a plurality of bendable protrusions formed in said lateral cutout portion of said base adjacent said archwire slot;
   (d) a removable archwire slot cover sized to cover said archwire slot, said removable archwire slot cover including tabs sized to matingly fit within said lateral cutout portions and said tabs of said cover being retained on said base by said bendable protrusions when bent toward said archwire slot so as to bear against said tabs of said slot cover and enable said bracket to function as a buccal tube, said removable archwire slot cover having ends outwardly flared in a direction away from said archwire slot, and being capable of being removed from said bracket base without removal of said bracket from said tooth surface by bending said protrusions away from said slot cover.

8. The bracket of claim 7 wherein said removable archwire slot cover extends longitudinally beyond said bottom and said opposite ends of said archwire slot so as to overhang said archwire slot when said removable archwire slot cover is retained on said base.

9. The bracket of claim 7 wherein said removable archwire slot cover is removable from said base by force applied to said removable archwire slot cover in a direction away from said bottom of said archwire slot to overcome the retention force provided by said protrusions.

10. An orthodontic bracket comprising:
(a) a base attachable to a tooth surface and extending outward away from said tooth surface said base including lateral cutout portions;
(b) an archwire slot formed within said base and sized to receive an archwire therewithin, said archwire slot having a bottom and two opposing sides adjacent said bottom and extending longitudinally between two opposite ends;
(c) a plurality of bendable protrusions formed in said lateral cutout portion of said base adjacent said archwire slot, said protrusions being adapted to bend selectively both toward and away from said archwire slot;
(d) a removable archwire slot cover sized to cover said archwire slot, said removable archwire slot cover having tabs adapted to matingly fit in said lateral cutout portions and said tabs of said cover being retained on said base by said bendable protrusions when bent toward said archwire slot over said tabs so as to cover said archwire slot and enable said bracket to function as a buccal tube, said removable archwire slot cover having ends outwardly flared in a direction away from said archwire slot; and,
(e) at least one pair of tie wings formed upon said base, each of said pair of tie wings having a first tie wing and a second tie wing oriented on opposite sides of said archwire slot from one another and each extending transversely away from said archwire slot, said first and second tie wings oriented and formed so as to permit use of a ligature or ligating module for holding said archwire within said archwire slot when said removable archwire slot cover is removed.

11. The bracket of claim 10 wherein said removable archwire slot cover extends longitudinally beyond said bottom and said opposite ends of said archwire slot so as to overhang said archwire slot when said removable archwire slot cover is secured onto said base.

* * * * *